US012691049B2

(12) United States Patent
Jaiser et al.

(10) Patent No.: US 12,691,049 B2
(45) Date of Patent: Jul. 28, 2026

(54) PROCESS FOR PRODUCING HAIR TREATMENT PRODUCTS BY MIXING ORGANIC $C_1$-$C_6$-ALKOXYSILANES AND ALKALIZING AGENTS IN SPECIFIC MOLAR RATIOS

(71) Applicant: Henkel AG & Co. KGaA, Duesseldorf (DE)

(72) Inventors: Phillip Jaiser, Langenfeld (DE); Torsten Lechner, Langenfeld (DE); Marc Nowottny, Mönchengladbach (DE); Juergen Schoepgens, Schwalmtal (DE); Carsten Mathiaszyk, Essen (DE); Avni Tairi, Antwerp (BE); Carolin Kruppa, Hilden (DE); Andreas Walter, Ratingen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 238 days.

(21) Appl. No.: 18/742,596

(22) Filed: Jun. 13, 2024

(65) Prior Publication Data

US 2024/0325271 A1 Oct. 3, 2024

Related U.S. Application Data

(63) Continuation of application No. PCT/EP2022/081290, filed on Nov. 9, 2022.

(30) Foreign Application Priority Data

Dec. 15, 2021 (DE) ........................ 102021214419.5

(51) Int. Cl.
*A61K 8/58* (2006.01)
*A61G 5/10* (2006.01)
*A61K 8/19* (2006.01)
*A61Q 5/10* (2006.01)

(52) U.S. Cl.
CPC ................ *A61K 8/585* (2013.01); *A61G 5/10* (2013.01); *A61K 8/19* (2013.01); *A61K 2800/432* (2013.01)

(58) Field of Classification Search
CPC .... A61K 8/585; A61K 8/19; A61K 2800/432; A61Q 5/10; A61Q 5/12; A61Q 5/065; C07F 7/0836; C07F 7/0872; C07F 7/1804; C07F 7/188
See application file for complete search history.

(56) References Cited

FOREIGN PATENT DOCUMENTS

| | | | |
|---|---|---|---|
| EP | 2168633 | B1 | 3/2016 |
| WO | 2020088814 | A1 | 5/2020 |
| WO | 2021018443 | A1 | 2/2021 |
| WO | 2021018444 | A1 | 2/2021 |
| WO | 2021018446 | A1 | 2/2021 |
| WO | WO2021018447 | A1 * | 2/2021 |

OTHER PUBLICATIONS

PCT International Search Report—WO PCT/EP2022/081290—Completed: Nov. 9, 2022; Mailing date: Mar. 15, 2023—Number of pp. 12.

* cited by examiner

*Primary Examiner* — Robert A Wax
*Assistant Examiner* — Kimberly Barber
(74) *Attorney, Agent, or Firm* — P. Scott Smith

(57) ABSTRACT

The present application relates to a process for producing a composition for treatment of keratinic material, especially human hair, comprising the blending of (a) one or more organic $C_1$-$C_6$-alkoxysilanes having one, two or three silicon atoms, with (b) one or more alkalizing agents, where the organic $C_1$-$C_6$-alkoxysilane(s) (a) is/are blended with an amount of alkalizing agent(s) (b) that corresponds to the molar amount of alkalizing agents determined by equation (G-1) where mol(alkalizing agent) represents the molar amount of alkalizing agent(s) used, mol(silanes) represents the total molar amount of the $C_1$-$C_6$-alkoxysilanes used in the reaction, n(alkoxy) represents the number of $C_1$-$C_6$-alkoxy groups per $C_1$-$C_6$-alkoxysilane, and S-Alkali represents an integer from 50 to 2000.

20 Claims, No Drawings

PROCESS FOR PRODUCING HAIR TREATMENT PRODUCTS BY MIXING ORGANIC $C_1$-$C_6$-ALKOXYSILANES AND ALKALIZING AGENTS IN SPECIFIC MOLAR RATIOS

BACKGROUND

The present application is in the field of cosmetics and relates to a process for producing hair treatment products. In the context of the process according to the invention, one or more organic $C_1$-$C_6$-alkoxysilanes are reacted with alkalizing agents in specific molar ratios.

A second subject matter is a composition for treatment of keratinic material—especially human hair—which has been produced according to the process described above.

A third subject matter of the present invention is the use of a composition which has been produced via the above-described process for treatment of keratinic material—especially for coloring keratinic material, and especially for coloring human hair.

Changing the shape and color of keratinous fibers, and in particular hair, represents an important area of modern cosmetics. To change the hair color, the skilled artisan is familiar with a variety of dyeing systems depending upon the dyeing requirements. Oxidation dyes are typically used for permanent, intense dyeing with good fastness properties and good gray coverage. Such dyes typically contain oxidation dye precursors, known as developer components, and coupler components, which together form the actual dyes under the influence of oxidizing agents—for example, hydrogen peroxide. Oxidation dyes are characterized by very long-lasting color results.

When using direct dyes, dyes which are already formed diffuse out of the dyeing agent into the hair fiber. In comparison with oxidative hair dyeing, the colors obtained with direct dyes have a lower durability and a more rapid washing out. Colors with direct dyes usually remain on the hair for a period of between 5 and 20 hair washes.

The use of color pigments for brief changes in color on the hair and/or the skin is known. Color pigments are generally understood to mean insoluble dyeing substances. These are present undissolved in the form of small particles in the dyeing formulation and are only deposited from the outside onto the hair fibers and/or the skin surface. They can therefore generally be removed again without leaving residue by washing a few times with surfactant-containing cleaning agents. Various products of this type by the name of hair mascara are available on the market.

If the user desires particularly long-lasting dyeing, the use of oxidative dyeing agents has hitherto been the only option. However, despite multiple optimization attempts, an unpleasant ammonia odor or amine odor cannot be completely avoided in oxidative hair dyeing. The hair damage that remains associated with the use of the oxidative dyeing agents also has a disadvantageous effect on the hair of the user.

EP 2168633 B1 addresses the task of producing long-lasting hair dyes using pigments. The document teaches that, when using a combination of pigment, organic silicon compound, hydrophobic polymer, and a solvent, dyeing can be produced on hair which is particularly resistant to being shampooed.

The organic silicon compounds used in EP 2168633 B1 are reactive compounds from the class of alkoxysilanes. These alkoxysilanes hydrolyze at high speed in the presence of water and form-depending upon the amounts of alkoxysilane and water used in each case-hydrolysis products and/or condensation products. The influence of the amount of water used in this reaction on the properties of the hydrolysis or condensation product is described, for example, in WO 2013068979 A2.

If these hydrolysis or condensation products are applied to keratinic material, a film or a coating is formed on the keratinic material, which completely surrounds the keratinic material and in this way greatly influences the properties of the keratinic material. Possible fields of application are, for example, permanent styling or also the permanent shape change of keratin fibers. In this case, the keratin fibers are mechanically brought into the desired shape and are then fixed in this form by forming the above-described coating. A further very particularly suitable application possibility is the coloring of keratinic material; in the context of this application, the coating or the film is produced in the presence of a coloring compound—for example, a pigment. The film dyed by the pigment remains on the keratinic material or the keratin fibers and results in surprisingly wash-fast dyeing.

The great advantage of the dyeing principle based upon alkoxysilanes is that the high reactivity of this compound class enables very rapid coating. Thus, extremely good coloring results can be achieved even after very short application periods of only a few minutes. In addition to these advantages, however, the high reactivity of the alkoxysilanes also entails some disadvantages. Thus, even slight changes in the production and application conditions, such as the change in humidity and/or temperature, can lead to severe fluctuations in the product performance. In particular, the work leading to this invention has shown that the alkoxysilanes react extremely sensitively to the conditions that prevail during the preparation of the keratin treatment agents.

Analytical studies have shown that, in the production of various silane mixtures and blends, complex hydrolysis and condensation reactions proceed which lead to oligomeric products of different molecular size depending upon the reaction conditions selected. In this context, it has been found that the molecular weight of these silane oligomers can have a great influence on the later product properties. If the wrong conditions are selected during the preparation, this can lead to the formation of excessively large or excessively small silane condensates, as a result of which the later product performance, and in particular the later coloring capability on the keratinic material, is adversely affected.

In order to accelerate or control the reaction, catalysts are often used in the hydrolysis and oligomerization of the $C_1$-$C_6$-alkoxysilanes. Suitable catalysts are known to the person skilled in the art from the prior art, but the general use of alkalizing agents as catalysts or reaction accelerators is also described in the documents of the prior art.

In the production processes known from the prior art, which proceed using alkalizing agents, it has been found to be problematic that the oligomeric silane blends produced via these processes were only very poorly removed from the reaction vessel or reactor after the reaction. Thus, after the reaction, the problem occurred that a portion of the reaction product had deposited in the form of a film on the reactor walls and was so resistant that the cleaning necessary after the reaction was very complicated and had to take place subject to a high consumption of cleaning agent. Such a contamination of the reactor that occurs after production is highly undesirable.

SUMMARY OF THE INVENTION

It was therefore the object of the present application to provide an optimized process for the production of hair treatment products based upon $C_1$-$C_6$-alkoxysilanes. The mixtures of $C_1$-$C_6$-alkoxysiloxanes contained in these compositions should be specifically produced such that the optimum performance properties are achieved in a subsequent application to keratinic material. At the same time, the synthesis reaction of the silane blends in the reaction vessel or reactor should be controllable such that the most complete removal of the reaction product is possible without a great loss of material, and that the reaction vessels or reactors are quickly ready for further production processes without time-consuming cleaning processes.

Surprisingly, it has now been found that the aforementioned object can be achieved in an excellent manner if the composition(s) for treatment of keratinic material are produced by blending reactive organic $C_1$-$C_6$-alkoxysilanes (a) with alkalizing agents (b) in very specific quantity ranges.

DETAILED DESCRIPTION OF THE INVENTION

A first subject matter of the present invention is a process for producing a composition for treatment of keratinic material—especially human hair—comprising the blending of (a) one or more organic $C_1$-$C_6$-alkoxysilanes having one, two, or three silicon atoms, with (b) one or more alkalizing agents, wherein the organic $C_1$-$C_6$-alkoxysilane(s) (a) is/are blended with an amount of alkalizing agent(s) (b) which corresponds to the molar amount of alkalizing agent determined according to the equation (G-1)

$$\text{mol(alkalizing agent)} = \frac{\text{mol(silanes)} \times n(\text{alkoxy})}{\text{S-Alkali}} \quad \text{(G-1)}$$

where mol(alkalizing agent) represents the total molar amount of the alkalizing agents used, mol(silanes) represents the total molar amount of the $C_1$-$C_6$-alkoxysilanes used, n(alkoxy) represents the number of $C_1$-$C_6$-alkoxy groups per $C_1$-$C_6$-alkoxysilane, and S-Alkali represents an integer from 50 to 2,000.

It has been found that a very uniform and resistant coating could be produced on the keratinic material or the hair with keratinic treatment compositions via this process according to the invention when applied to keratinic material—especially human hair. This coating proved to be extremely robust against external influences such as shampooings, frictions such as arise, for example, in contact with textiles and combing, and UV light. At the same time, these keratinic treatment compositions could be removed very well and easily from the reaction vessels in which they were produced without stubborn, polymeric conglomerates depositing on the walls of the reactor, and without the reaction vessels having to be subjected to complex cleaning.

Agent for Treating Keratinic Material

Keratinic material is understood to mean hair, skin, and nails (such as, for example, fingernails and/or toenails). Furthermore, wool, furs, and feathers also fall under the definition of the keratinic material.

Keratinic material is preferably understood to be human hair, human skin, and human nails, and in particular fingernails and toenails. Keratinic material is very particularly preferably understood to mean human hair.

Agents for treating keratinic material are understood to mean, for example, agents for coloring keratinic material, agents for reshaping or shaping keratinic material, and in particular keratin fibers, or else agents for the conditioning or for the care of the keratinic material. The compositions produced by the process according to the invention exhibit especially good suitability for coloring keratinic material-especially for coloring keratin fibers, which are especially preferably human hair.

In the context of this invention, the term, "agent for coloring," is used for a coloring of the keratinic material, and in particular of hair, caused by use of coloring compounds, such as thermochromic and photochromic dyes, pigments, mica, direct dyes, and/or oxidation dyes. In this dyeing, the aforementioned coloring compounds are deposited in a particularly homogeneous and smooth film on the surface of the keratinic material or diffuse into the keratin fibers. The film forms in situ by oligomerization or condensation of the organic silicon compounds, wherein the coloring compound(s) interact with this film or this coating, or are incorporated therein.

By blending one or more organic $C_1$-$C_6$-alkoxysilanes (a) with the alkalizing agent(s) (b), a blend of hydrolyzed and condensed $C_1$-$C_6$-alkoxysilanes is produced, which can also be referred to as a silane blend. The silane blend is component of the keratinic treatment compositions according to the invention. In the application, the silane blend can either be applied as such on the keratinic materials, or else blended with one or more further compositions before application, so that a ready-to-use keratinic treatment composition is first produced by blending with the further formulation(s).

Process for Producing the Keratinic Treatment Compositions

The production of the mixture of organic $C_1$-$C_6$-alkoxysilanes (a) and alkalizing agents (b) preferably takes place according to the invention in a reactor or reaction vessel suited for this purpose. A reaction vessel which is very well suited for smaller batches is, for example, a glass flask having a capacity of 1 liter, 3 liters, or 5 liters, typically used for chemical reactions—for example, a 3-liter, single-neck, or multi-neck flask with ground joints.

A delimited space (container, vessel) which has been specially designed and produced to allow for and be able to control a processing of reactions determined therein under defined conditions is referred to as a reactor.

For larger batches, it has been found to be advantageous to carry out the reaction in reactors made of metal. Typical reactors can comprise, for example, a filling quantity of 10 liters, 20 liters, or 50 liters. Larger reactors for production scale can also comprise filling quantities of 100 liters, 500 liters, or 1,000 liters.

Double-wall reactors have two reactor shells or reactor walls, wherein a temperature control liquid can circulate in the region located between the two walls. This enables a particularly good setting of the temperature to the required values.

The use of reactors, and in particular double wall reactors with an increased heat exchange surface, has also proven to be particularly suitable, wherein the heat exchange can take place either via internal fittings or else by using an external heat exchanger.

Corresponding reactors are, for example, laboratory reactors from IKA. In this context, the "LR-2.ST" models or the "magic plant" model can be mentioned.

Further reactors which can be used are reactors with thin-film evaporators, because a very good heat dissipation and thus a particularly exact temperature control can be carried out in this way. Thin-film evaporators are alternatively also referred to as thin-layer evaporators. Thin-film evaporators can be purchased commercially, for example, from Asahi Glassplant, Inc.

All of these aforementioned reaction vessels and reactor types can be cleaned especially well after application of the production process according to the invention.

Blending of One or More $C_1$-$C_6$-Alkoxysilanes (a)

The production process according to the invention for treatment of keratinic material—especially human hair—comprises blending one or more organic $C_1$-$C_6$-alkoxysilanes having one, two, or three silicon atoms (a) with one or more alkalizing agents (b).

The organic $C_1$-$C_6$-alkoxysilanes are organic, non-polymeric silicon compounds, which are preferably selected from the group of silanes having one, two, or three silicon atoms.

Organic silicon compounds, which are alternatively also referred to as organosilicon compounds, are compounds which either have a direct silicon-carbon bond (Si—C) or in which the carbon is linked to the silicon atom via an oxygen, nitrogen, or sulfur atom. The organosilicon compounds according to the invention are compounds which contain one to three silicon atoms. The organic silicon compounds particularly preferably contain one or two silicon atoms.

According to the IUPAC rules, the designation, "silane," denotes a substance group of chemical compounds based upon a silicon backbone and hydrogen. In the case of organic silanes, the hydrogen atoms are replaced, completely or in part, by organic groups such as (substituted) alkyl groups and/or alkoxy groups.

Characteristic of the $C_1$-$C_6$-alkoxysilanes according to the invention is that at least one $C_1$-$C_6$-alkoxy group is present directly bound to a silicon atom. The $C_1$-$C_6$-alkoxysilanes according to the invention thus comprise at least one structural unit R'R"R'"Si—O—($C_1$-$C_6$-alkyl), the groups R', R", and R'" representing the three other binding valences of the silicon atom.

The or these $C_1$-$C_6$-alkoxy groups bonded to the silicon atom are very reactive and are hydrolyzed at high speed in the presence of water, the reaction rate, inter alia, also depending upon the number of hydrolyzable groups per molecule. If the hydrolyzable $C_1$-$C_6$-alkoxy group is an ethoxy group, the organic silicon compound thus preferably contains a structural unit R'R"R'"Si—O—CH2-CH3. The groups R', R", and R'" again represent the three remaining free valences of the silicon atom.

Very particularly good results were able to be obtained when $C_1$-$C_6$-alkoxysilanes of the formula (I) and/or (II) were used in the process according to the invention.

In a further very particularly preferred embodiment, a process according to the invention is characterized by blending one or more organic $C_1$-$C_6$-alkoxysilanes (a) of formula (I) and/or (II) with alkalizing agents (b), $$R_1R_2N—L—Si(OR_3)_a(R_4)_b \quad (I)$$

where $R_1$, $R_2$ represent, independently of one another, a hydrogen atom or a $C_1$-$C_6$-alkyl group, L represents a linear or branched, divalent $C_1$-$C_{20}$-alkylene group, $R_3$, $R_4$ represent, independently of one another, a $C_1$-$C_6$-alkyl group, a represents an integer from 1 to 3, and b represents the integer 3-a, and $$(R_5O)_c(R_6)_dSi—(A)_e—[NR_7—(A')]_f—[O—(A'')]_g—[NR_8—(A''')]_h—Si(R_6')_{d'}(OR_5')_{c'}, \quad (II)$$

where

R5, R5', R5", R6, R6', and R6" represent, independently of one another, a $C_1$-$C_6$-alkyl group, A, A', A", A'", and A"" represent, independently of one another, a linear or branched, divalent $C_1$-$C_{20}$-alkylene group, $R_7$ and $R_8$ represent, independently of one another, a hydrogen atom, a $C_1$-$C_6$-alkyl group, a hydroxy $C_1$-$C_6$-alkyl group, a $C_2$-$C_6$-alkenyl group, an amino $C_1$-$C_6$-alkyl group, or a group of formula (III), $$(A'''')—Si(R_6'')_{d''}(OR_5'')_{c''}, \quad (III)$$

c, represents an integer from 1 to 3,
d represents the integer 3-c,
c' represents an integer from 1 to 3,
d' represents the integer 3-c',
c" represents an integer from 1 to 3,
d" represents the integer 3-c",
e represents 0 or 1,
f represents 0 or 1,
g represents 0 or 1,
h represents 0 or 1,
with the proviso that at least one of the groups e, f, g, and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A, A', A", A'", and A"" in the compounds of formula (I) and (II) are explained by way of example below:

Examples of a $C_1$-$C_6$-alkyl group are the methyl, ethyl, propyl, isopropyl, n-butyl, s-butyl, and t-butyl, n-pentyl, and n-hexyl groups. Propyl, ethyl, and methyl are preferred alkyl groups. Examples of a $C_2$-$C_6$-alkenyl group are vinyl, allyl, but-2-enyl, but-3-enyl, and isobutenyl; preferred $C_2$-$C_6$-alkenyl groups are vinyl and allyl. Preferred examples of a hydroxy-$C_1$-$C_6$-alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino-$C_1$-$C_6$ alkyl group are the aminomethyl group, the 2-aminoethyl group, and the 3-aminopropyl group. The 2-aminoethyl group is particularly preferred. Examples of a linear divalent $C_1$-$C_{20}$-alkylene group are, for example, the methylene group (—$CH_2$—), the ethylene group (—$CH_2$—$CH_2$—), the propylene group (—$CH_2$—$CH_2$—$CH_2$—), and the butylene group ($CH_2$—$CH_2$—$CH_2$—$CH_2$—). The propylene group (—$CH_2$—$CH_2$—$CH_2$—) is particularly preferred. Starting at a chain length of 3 C atoms, divalent alkylene groups may also be branched. Examples of branched, divalent $C_3$-$C_{20}$-alkylene groups are (—$CH_2$—$CH(CH_3)$—) and (—$CH_2$—$CH(CH_3)$—$CH_2$—).

In the organosilicon compound of formula (I)

$$R_1R_2N—L—Si(OR_3)_a(R_4)_b, \quad (I)$$

the groups $R_1$ and $R_2$ represent, independently of one another, a hydrogen atom or a $C_1$-$C_6$-alkyl group. Very particularly preferably, the groups $R_1$ and $R_2$ both represent a hydrogen atom.

The structural unit or the linker -L-, which represents a linear or branched, divalent $C_1$-$C_{20}$-alkylene group, is located in the middle part of the organic silicon compound. The divalent $C_1$-$C_{20}$-alkylene group can alternatively also be designated a divalent $C_1$-$C_{20}$-alkylene group, which means that each -L- grouping can enter into two bonds.

Preferably, -L- represents a linear, divalent $C_1$-$C_{20}$-alkylene group. Further preferably, -L- represents a linear divalent $C_1$-$C_6$ alkylene group. Particularly preferably, -L- represents a methylene group ($—CH_2—$), an ethylene group ($—CH_2—CH_2—$), a propylene group ($—CH_2—CH_2—CH_2—$), or a butylene group ($—CH_2—CH_2—CH_2—CH_2—$). Very particularly preferably, L represents a propylene group ($—CH_2—CH_2—CH_2—$).

The organosilicon compounds according to the invention of formula (I)

$$R_1R_2N—L—Si(OR_3)_a(R_4)_b, \quad (I)$$

each bear one end of the silicon-containing grouping $—Si(OR_3)_a(R_4)_b$.

In the terminal structural unit $—Si(OR_3)_a(R_4)_b$, the $R_3$ and $R_4$ groups each independently represent a $C_1$-$C_6$-alkyl group. Particularly preferably, $R_3$ and $R_4$ represent, independently of one another, a methyl group or an ethyl group.

In this case, a represents an integer from 1 to 3, and b represents the integer 3-a. If a represents the number 3, then b is equal to 0. If a represents the number 2, then b is equal to 1. If a represents the number 1, then b is equal to 2.

It was possible to produce a keratinic treatment composition having especially good properties when in step (1) at least one organic $C_1$-$C_6$-alkoxysilane of formula (I) was mixed with water or brought to the reaction, in which the groups $R_3$, $R_4$, independently of one another, represent a methyl group or an ethyl group.

Furthermore, it was possible to obtain colorings having the best wash fastness when in step (1) at least one organic $C_1$-$C_6$-alkoxysilane of formula (I) was reacted with water, in which the group a represents the number 3. In this case, the group b represents the number 0.

In a further preferred embodiment, a process according to the invention is characterized in that one or more organic $C_1$-$C_6$-alkoxysilanes (a) of the formula (I) is/are blended with alkalizing agents (b), where $R_3$, $R_4$ represent, independently of one another, a methyl group or an ethyl group, and a represents the number 3, and b represents the number 0.

To achieve the object according to the invention, particularly well-suited organosilicon compounds of formula (I) are:

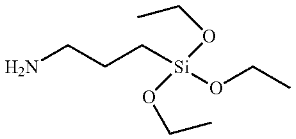
, (3-aminopropyl)triethoxysilane

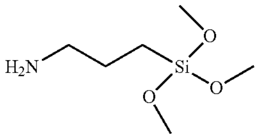

(3-aminopropyl)trimethoxysilane,

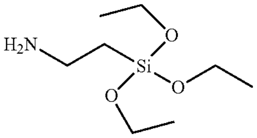
, (2-aminoethyl)triethoxysilane

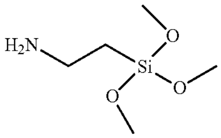

(2-aminoethyl)trimethoxysilane,

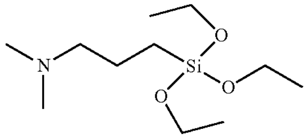

(3-dimethylaminopropyl)triethoxysilane,

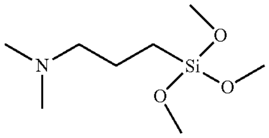

(3-dimethylaminopropyl)trimethoxysilane,

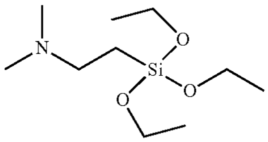

(2-dimethylaminoethyl)triethoxysilane,

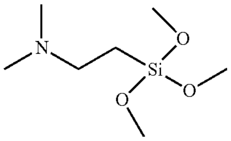

(2-dimethylaminoethyl)trimethoxysilane, and/or

In a further preferred embodiment, a process according to the invention is characterized in that one or more organic $C_1$-$C_6$-alkoxysilanes (a) selected from the group consisting of (3-aminopropyl)triethoxysilane,
(3-aminopropyl)trimethoxysilane,
1-(3-aminopropyl)silanetriol,
(2-aminoethyl)triethoxysilane,
(2-aminoethyl)trimethoxysilane,
1-(2-aminoethyl)silanetriol,
(3-dimethylaminopropyl)triethoxysilane,
(3-dimethylaminopropyl)trimethoxysilane, 1-(3-dimethylaminopropyl)silanetriol,
(2-dimethylaminoethyl)triethoxysilane,
(2-dimethylaminoethyl)trimethoxysilane, and/or
1-(2-dimethylaminoethyl)silanetriol
are blended or reacted with alkalizing agent (b).

The terms, blend and mix, may be used synonymously for the purposes of the present application. (a) and (b) are reacted with one another upon blending or mixing.

The aforementioned organic silicon compounds of the formula (I) are commercially available. (3-aminopropyl) trimethoxysilane can be purchased from Sigma-Aldrich, for example. (3-aminopropyl)triethoxysilane is commercially available from Sigma-Aldrich.

In the context of a further embodiment of the process according to the invention, one or more organic $C_1$-$C_6$-alkoxysilanes (a) of formula (II) can be blended or reacted with alkalizing agent (b), $$(R_5O)_c(R_6)_dSi—(A)_e—[NR_7—(A')]_f—[O—(A'')]_g—[NR_8—(A''')]_h—Si(R_6')_{d'}(OR_5')_{c'}. \quad (II)$$

The organosilicon compounds of formula (II) according to the invention each bear the silicon-containing groups $(R_5O)_c(R_6)_dSi$— and $$—Si(R_6')_{d'}(OR_5')_{c'}$$

at their two ends.

The groups -$(A)_e$- and —$[NR_7$-$(A')]_f$- and —$[O$-$(A'')]_g$- and —$[NR_8$-$(A''')]_h$- are in the middle part of the molecule of formula (II). In this case, each of the groups e, f, g, and h can represent, independently of one another, the number 0 or 1, there being the proviso that at least one of the groups e, f, g, and h is different from 0. In other words, an organosilicon compound of formula (II) according to the invention contains at least one grouping from the group consisting of -(A)- and —$[NR_7$-$(A')]$- and —$[O$-$(A'')]$- and —$[NR_8$-$(A''')]$-.

In the two terminal structural units $(R_5O)_c(R_6)_dSi$— and $$—Si(R_6')_{d'}(OR_5')_{c'},$$

the groups R5, R5', R5" represent, independently of one another, a $C_1$-$C_6$-alkyl group. The groups R6, R6', and R6" represent, independently of one another, a $C_1$-$C_6$-alkyl group.

In this case, c represents an integer from 1 to 3, and d represents the integer 3-c. If c represents the number 3, then d is equal to 0. If c represents the number 2, then d is equal to 1. If c represents the number 1, then d is equal to 2.

Similarly, c' represents an integer from 1 to 3, and d' represents the integer 3-c'. If c' represents the number 3, then d' is equal to 0. If c' represents the number 2, then d' is equal to 1. If c' represents the number 1, then d' is equal to 2.

Dyes having the best wash fastness were able to be obtained when the groups c and c' both represent the number 3. In this case, d and d' both represent the number 0.

In a further preferred embodiment, a process according to the invention is characterized in that one or more organic $C_1$-$C_6$-alkoxysilanes (a) of formula (II) is/are blended or reacted with alkalizing agents (b), $$(R_5O)_c(R_6)_dSi—(A)_e—[NR_7—(A')]_f—[O—(A'')]_g—[NR_8—(A''')]_h—Si(R_6')_{d'}(OR_5')_{c'}, \quad (II)$$

where

R5 and R5' represent, independently of one another, a methyl group or an ethyl group, c and c' both represent the number 3, and d and d' both represent the number 0.

If c and c' both represent the number 3, and d and d' both represent the number 0, the organosilicon compound according to the invention of formula (Ha) corresponds to:

$$(R_5O)_3Si—(A)_e—[NR_7—(A')]_f—[O—(A'')]_g—[NR_8—(A''')]_h—Si(OR_5')_3. \quad (IIa)$$

The groups e, f, g, and h can represent, independently of one another, the number 0 or 1, at least one group from e, f, g, and h being different from zero. The abbreviations e, f, g, and h therefore define which of the groupings -$(A)_e$- and —$[NR_7$-$(A')]_f$- and —$[O$-$(A'')]_g$ and —$[NR_8$-$(A''')]_h$- are located in the middle part of the organic silicon compound of formula (II).

In this context, the presence of certain groupings has proven to be particularly advantageous with regard to achieving wash-fast dyeing results. Particularly good results could be obtained if at least two of the groups e, f, g, and h represent the number 1. Very particularly preferably, e and f both represent the number 1. Furthermore, g and h very particularly preferably both represent the number 0.

If e and f both represent the number 1, and g and h both represent the number 0, the organosilicon compound according to the invention corresponds to formula (IIb):

$$(R_5O)_c(R_6)_dSi—(A)—[NR_7—(A')]—Si(R_6')_{d'}(OR_5')_{c'}. \quad (IIb)$$

The groups A, A', A", A"', and A"" represent, independently of one another, a linear or branched, divalent $C_1$-$C_{20}$-alkylene group. The groups A, A', A", A"', and A"" preferably represent, independently of one another, a linear, divalent $C_1$-$C_{20}$-alkylene group. More preferably, the groups A, A', A", A"', and A"" represent, independently of one another, a linear, divalent $C_1$-$C_6$ alkylene group.

The divalent $C_1$-$C_{20}$-alkylene group can alternatively also be designated a divalent $C_1$-$C_{20}$-alkylene group, which means that each grouping A, A', A", A"', and A"" can enter two bonds.

Particularly preferably, the groups A, A', A", A'", and A"" represent, independently of one another, a methylene group ($-CH_2-$), an ethylene group ($-CH_2-CH_2-$), a propylene group ($-CH_2-CH_2-CH_2-$), or a butylene group ($-CH_2-CH_2-CH_2-CH_2-$). Very particularly preferably, the groups A, A', A", A'", and A"" represent a propylene group ($-CH_2-CH_2-CH_2-$).

If the functional group f represents the number 1, the organosilicon compound of formula (II) according to the invention contains a structural group $-[NR_7-(A')]-$.

If the functional group h represents the number 1, the organosilicon compound of formula (II) according to the invention contains a structural group $-[NR_8-(A''')]-$.

In this context, $R_7$ and $R_8$ represent, independently of one another, a hydrogen atom, a $C_1$-$C_6$-alkyl group, a hydroxy $C_1$-$C_6$-alkyl group, a $C_2$-$C_6$-alkenyl group, an amino $C_1$-$C_6$-alkyl group, or a group of formula (III):

$$-(A'''')-Si(R_6'')_{d''}(OR_5'')_{c''}. \quad \text{(III)}$$

Most preferably, the functional groups $R_7$ and $R_8$ represent, independently of one another, a hydrogen atom, a methyl group, a 2-hydroxyethyl group, a 2-alkenyl group, a 2-aminoethyl group, or a grouping of formula (III).

If the group f represents the number 1, and the group h represents the number 0, the organic silicon compound according to the invention contains the grouping-$[NR_7-(A')]$, but not the grouping $-[NR_8-(A''')]$. If the functional group $R_7$ represents a grouping of formula (III), the pretreatment agent (a) contains an organosilicon compound with 3 reactive silane groups.

To achieve the object according to the invention, suitable organosilicon compounds of formula (II) are:

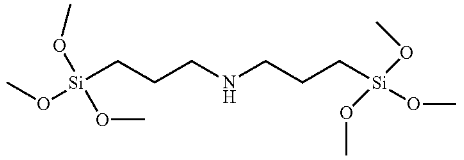

3-(trimethoxysilyl)-N-[3-(trimethoxysilyl)propyl]-1-propanamine,

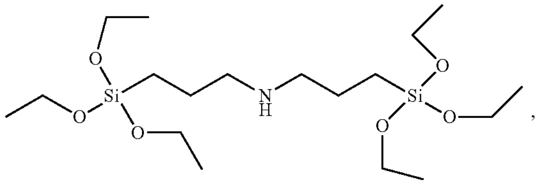

3-(triethoxysilyl)-N-[3-(triethoxysilyl)propyl]-1-propanamine

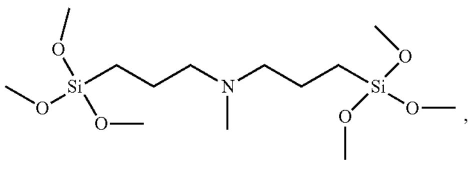

N-methyl-3-(trimethoxysilyl)-N-[3-(trimethoxysilyl)propyl]-1-propanamine

-continued

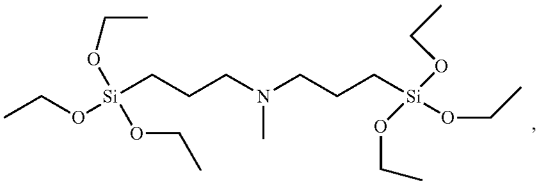

N-methyl-3-(triethoxysilyl)-N-[3-(triethoxysilyl)propyl]-1-propanamine

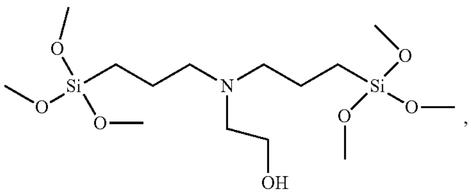

2-[bis[3-(trimethoxysilyl)propyl]amino]-ethanol

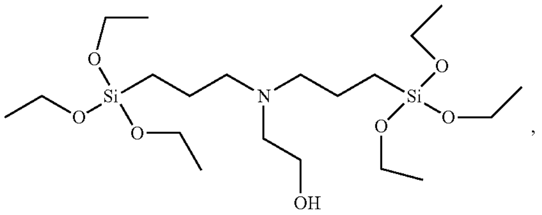

2-[bis[3-(triethoxysilyl)propyl]amino]ethanol

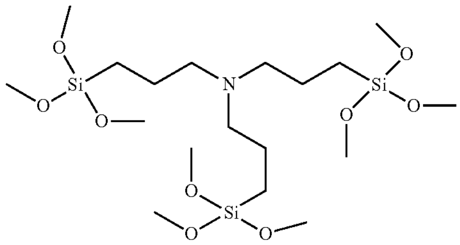

3-(trimethoxysilyl)-N,N-bis[3-(trimethoxysilyl)propyl]-1-propanamine,

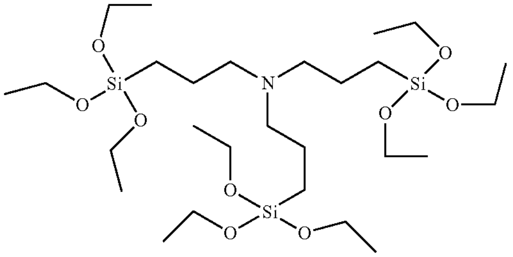

3-(triethoxysilyl)-N,N-bis[3-(triethoxysilyl)propyl]-1-propanamine,

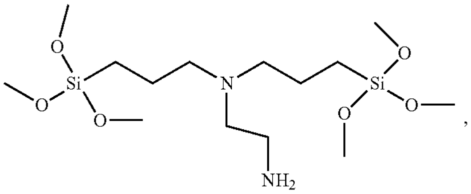

N1,N1-bis[3-(trimethoxysilyl)propyl]-1,2-ethanediamine

-continued

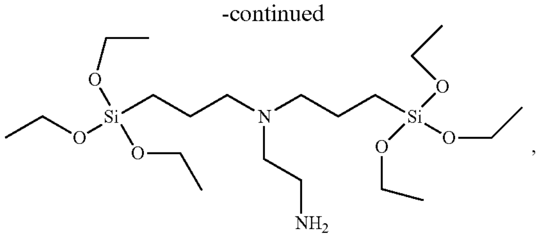

N1,N1-bis[3-(triethoxysilyl)propyl]-1,2-ethanediamine

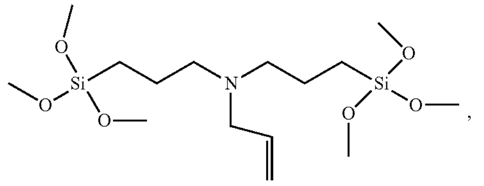

N,N-bis[3-(trimethoxysilyl)propyl]-2-propen-1-amine

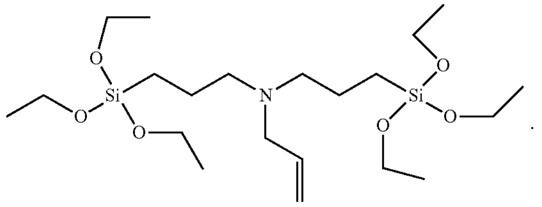

N,N-bis[3-(triethoxysilyl)propyl]-2-propen-1-amine

The aforementioned organosilicon compounds of formula (II) are commercially available.

Bis(trimethoxysilylpropyl)amines having the CAS number 82985-35-1 can, for example, be purchased from Sigma-Aldrich.

Bis[3-(triethoxysilyl)propyl]amines having the CAS number 13497-18-2 can be purchased from Sigma-Aldrich, for example.

N-methyl-3-(trimethoxysilyl)-N-[3-(trimethoxysilyl)propyl]-1-propanamine is alternatively also referred to as bis(3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine having the CAS number 18784-74-2 can be purchased, for example, from Fluorochem or Sigma-Aldrich.

In another preferred embodiment, a process according to the invention is characterized in that one or more organic $C_1$-$C_6$-alkoxysilanes (a) of formula (II) which are selected from the group consisting of 3-(trimethoxysilyl)-N-[3-(trimethoxysilyl)propyl]-1-propanamine,
3-(triethoxysilyl)-N-[3-(triethoxysilyl)propyl]-1-propanamine,
N-methyl-3-(trimethoxysilyl)-N-[3-(trimethoxysilyl)propyl]-1-propanamine,
N-methyl-3-(triethoxysilyl)-N-[3-(triethoxysilyl)propyl]-1-propanamine,
2-[bis[3-(trimethoxysilyl)propyl]amino]ethanol,
2-[bis[3-(triethoxysilyl)propyl]amino]ethanol,
3-(trimethoxysilyl)-N,N-bis[3-(trimethoxysilyl)propyl]-1-propanamine,
3-(triethoxysilyl)-N,N-bis[3-(triethoxysilyl)propyl]-1-propanamine,
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine, and/or
N,N-bis[3-(triethoxysilyl)propyl]-2-propen-1-amine, are blended with or brought to reaction with alkalizing agents (b).

In further dyeing tests, it has likewise been found to be very particularly advantageous if at least one organic $C_1$-$C_6$-alkoxysilane of formula (IV) was used in the process according to the invention $$R_9Si(OR_{10})_k(R_{11})_m, \tag{IV}$$

The compounds of formula (IV) are organosilicon compounds selected from silanes having one, two, or three silicon atoms, wherein the organosilicon compound comprises one or more hydrolyzable groups per molecule.

The organic silicon compound(s) of the formula (IV) can also be designated silanes of the type of the alkyl $C_1$-$C_6$ alkoxy-silanes, $$R_9Si(OR_{10})_k(R_{11})_m, \tag{IV}$$

where $R_9$ represents a $C_1$-$C_{12}$-alkyl group,
$R_{10}$ represents a $C_1$-$C_6$-alkyl group,
$R_{11}$ represents a $C_1$-$C_6$-alkyl group,
k represents an integer from 1 to 3, and
m represents the integer 3-k.

In a further embodiment, an especially preferred process according to the invention is characterized by the blending of one or more organic $C_1$-$C_6$-alkoxysilanes (a) of formula (IV) with alkalizing agent (b), $$R_9Si(OR_{10})_k(R_{11})_m \tag{IV},$$

where $R_9$ represents a $C_1$-$C_{12}$-alkyl group,
$R_{10}$ represents a $C_1$-$C_6$-alkyl group,
$R_{11}$ represents a $C_1$-$C_6$-alkyl group,
k represents an integer from 1 to 3, and
m represents the integer 3-k.

In the organic $C_1$-$C_6$-alkoxysilanes of the formula (IV), the group $R_9$ represents a $C_1$-$C_{12}$-alkyl group. This $C_1$-$C_{12}$-alkyl group is saturated and can be linear or branched. $R_9$ preferably represents a $C_1$-$C_8$-alkyl group. Preferably, $R_9$ represents a methyl group, an ethyl group, an n-propyl group, an n-butyl group, an n-pentyl group, an n-hexyl group, an n-octyl group, or an n-dodecyl group. Particularly preferably, $R_9$ represents a methyl group, an ethyl group, or an n-octyl group.

In the organosilicon compounds of formula (IV), the group $R_{10}$ represents a $C_1$-$C_6$-alkyl group. Particularly preferably, $R_{10}$ represents a methyl group or an ethyl group.

In the organosilicon compounds of formula (IV), the group $R_{11}$ represents a $C_1$-$C_6$-alkyl group. Especially preferably, $R_{11}$ represents a methyl group or an ethyl group.

Furthermore, k represents an integer from 1 to 3, and m represents the integer 3-k. If k represents the number 3, then m is equal to 0. If k represents the number 2, then m is equal to 1. If k represents the number 1, then m is equal to 2.

It was possible to obtain colorings with the best wash-fastnesses when, during the production of the preparation according to the invention, at least one organosilicon compound of formula (IV) was used in which the functional group k represents the number 3. In this case, the group m represents the number 0.

To achieve the object according to the invention, particularly well-suited organosilicon compounds of formula (IV) are:

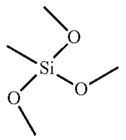

methyltrimethoxysilane

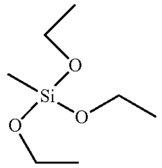

methyltriethoxysilane,

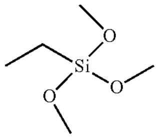

ethyltrimethoxysilane,

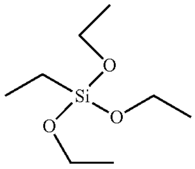

ethyltriethoxysilane,

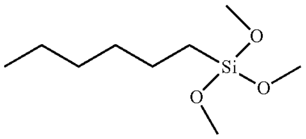

n-hexyltrimethoxysilane (also referred to as hexyltrimethoxysilane),

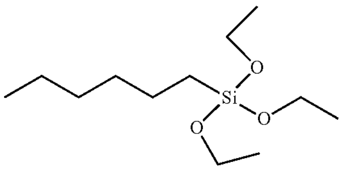

n-hexyltriethoxysilane (also referred to as hexyltriethoxysilane),

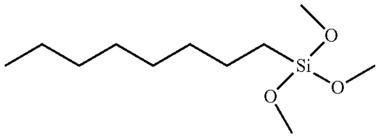

n-octyltrimethoxysilane (also referred to as octyltrimethoxysilane),

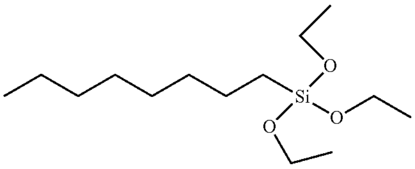

n-octyltriethoxysilane (also referred to as octyltriethoxysilane),

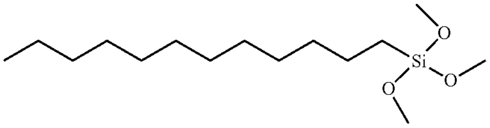

, and/or n-dodecyltrimethoxysilane
(also referred to as dodecyltrimethoxysilane)

-continued

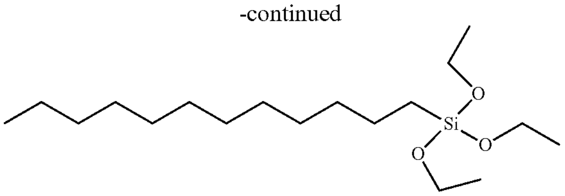

.

n-dodecyltriethoxysilane (also referred to as dodecyltriethoxysilane)

In a further preferred embodiment, a process according to the invention is characterized in that one or more organic $C_1$-$C_6$-alkoxysilanes (a) selected from the group consisting of (3-aminopropyl)triethoxysilane,
(3-aminopropyl)trimethoxysilane,
(2-aminoethyl)triethoxysilane,
(2-aminoethyl)trimethoxysilane,
(3-dimethylaminopropyl)triethoxysilane,
(3-dimethylaminopropyl)trimethoxysilane,
(2-dimethylaminoethyl)triethoxysilane,
(2-dimethylaminopropyl)trimethoxysilane,
methyltrimethoxysilane,
methyltriethoxysilane,
ethyltrimethoxysilane,
ethyltriethoxysilane,
hexyltrimethoxysilane,
hexyltriethoxysilane,
octyltrimethoxysilane,
octyltriethoxysilane,
dodecyltrimethoxysilane,
dodecyltriethoxysilane,
vinyltrimethoxysilane,
vinyltriethoxysilane,
tetramethoxysilane, and
tetraethoxysilane are blended with the alkalizing agent(s) (b).

Furthermore, it has been found to be very particularly preferred in the process according to the invention to blend at least one organic $C_1$-$C_6$-alkoxysilane (a1) of formula (I) and at least one organic $C_1$-$C_6$-alkoxysilane (a2) of formula (IV) with alkalizing agent (b). In this way, the hydrolysis or condensation reaction of the organic $C_1$-$C_6$-alkoxysilanes (a1) and (a2) is started in a targeted manner and controlled.

The reaction taking place of the organic $C_1$-$C_6$-alkoxysilane(s) (a) with the alkalizing agent(s) (b) can take place in various ways. The reaction starts as soon as the $C_1$-$C_6$-alkoxysilanes come into contact with alkalizing agents by blending or mixing. One possibility is to initially add the desired amount of alkalizing agent (b)—as applicable, in the present case, a specific amount of water—in the reaction vessel or reactor, and then to add the $C_1$-$C_6$-alkoxysilanes (a).

In a further embodiment, it is also possible to first provide the organic $C_1$-$C_6$-alkoxysilanes in the reaction vessel or reactor (a) and then add the desired amount of one or more alkalizing agents (b). Also within the scope of this embodiment, the alkalizing agent(s) (b) can be added in the form of a mixture of alkalizing agent (b) and water to the $C_1$-$C_6$-alkoxysilanes (a).

Blending of (a) with One or More Alkalizing Agents (b)

In the production process according to the invention, the above-described organic $C_1$-$C_6$-alkoxysilane(s) (a) is/are blended with one or more alkalizing agents (b). When (a) and (b) are blended, the hydrolysis and the subsequent oligomerization or condensation of the $C_1$-$C_6$-alkoxysilanes starts; in other words, the addition of the alkalizing agents (b) causes an initiation and acceleration of the hydrolysis or condensation reaction.

The alkalizing agents (b) are selected from the group of inorganic and/or organic bases.

Most particularly, the alkalizing agent(s) (b) is/are selected from the group consisting of sodium hydroxide, potassium hydroxide, magnesium hydroxide, calcium hydroxide, and ammonia. Sodium hydroxide and potassium hydroxide are very particularly preferred.

In a further especially preferred embodiment, a process according to the invention is characterized in that the organic $C_1$-$C_6$-alkoxysilane(s) (a) is/are mixed with one or more alkalizing agents (b) selected from the group consisting of sodium hydroxide, potassium hydroxide, lithium hydroxide, magnesium hydroxide, calcium hydroxide, and ammonia.

Furthermore, further inorganic alkalizing agents or bases can also be used. According to the invention, further usable, inorganic alkalizing agents can preferably selected, for example, from the group which is formed from sodium phosphate, potassium phosphate, sodium silicate, sodium metasilicate, potassium silicate, sodium carbonate, and potassium carbonate.

Alkanolamines and/or basic amino acids can be used as the alkalizing agent (b) from the group of organic bases, for example.

Alkanolamines can be selected from primary amines having a $C_2$-$C_6$-alkyl basic structure that carries at least one hydroxyl group. Preferred alkanolamines are selected from the group which is formed of 2-aminoethan-1-ol (monoethanolamine), 3-aminopropan-1-ol, 4-aminobutan-1-ol, 5-amino-pentan-1-ol, 1-aminopropan-2-ol, 1-aminobutan-2-ol, 1-amino-pentan-2-ol, 1-amino-pentan-3-ol, 1-amino-pentan-4-ol, 3-amino-2-methylpropan-1-ol, 1-amino-2-methylpropan-2-ol, 3-aminopropane-1,2-diol, and 2-amino-2-methyl propane-1,3-diol.

An amino acid within the meaning of the invention is an organic compound which contains at least one protonatable amino group and at least one —COOH or one —$SO_3H$ group in its structure. Preferred amino acids are aminocarboxylic acids, and in particular α-(alpha)-aminocarboxylic acids and ω-aminocarboxylic acids, with α-aminocarboxylic acids being particularly preferred.

According to the invention, basic amino acids are understood to mean the amino acids which have an isoelectric point pI greater than 7.0.

Basic α-aminocarboxylic acids contain at least one asymmetric carbon atom. In the context of the present invention, both possible enantiomers can equally be used as a specific compound or else mixtures thereof—in particular, as racemates. However, it is particularly advantageous to use the naturally occurring isomer form, usually in the L configuration.

The basic amino acids are preferably selected from the group which is formed of arginine, lysine, ornithine, and histidine, and more preferably of arginine and lysine. In another well-suited embodiment, a process according to the invention is therefore characterized in that a basic amino acid from the group consisting of arginine, lysine, ornithine, and/or histidine is used as an alkalizing agent (b).

Blending (a) and (b) in Specific Molar Ratios

It is essential to the invention for the production process according to the invention to blend the organic $C_1$-$C_6$-alkoxysilane(s) (a) with the alkalizing agent(s) (b) in very specific molar ratios. By maintaining these specific molar ratios, the oligomerization and condensation reaction can be controlled in such a way that, on the one hand, the reactor vessels are easy to clean after the reaction, but, on the other, also keratinic treatment compositions having good performance properties can be produced.

The amount of the alkalizing agent (b) used in the production process is indicated in mol and corresponds to the molar amount of alkalizing agent which is determined according to the equation (G-1)

$$\text{mol(alkalizing agent)} = \frac{\text{mol(silanes)} \times n(\text{alkoxy})}{\text{S-Alkali}} \qquad \text{(G-1)}$$

where mol(alkalizing agent) represents the total molar amount of the alkalizing agents used, mol(silanes) represents the total molar amount of the $C_1$-$C_6$-alkoxysilanes used, n(alkoxy) represents the number of $C_1$-$C_6$-alkoxy groups per $C_1$-$C_6$-alkoxysilane, and S-Alkali represents an integer from 50 to 2,000.

The variable mol(alkalizing agent) is the total molar amount of alkalizing agent (b) which is used in the production process according to the invention and which is blended with the organic $C_1$-$C_6$-alkoxysilanes (a).

mol(silanes) represents the total molar amount of the $C_1$-$C_6$-alkoxysilanes used in the reaction. If only a $C_1$-$C_6$-alkoxysilane (a) of a particular structure is used, the total molar amount mol(silanes) corresponds to the molar amount of mol(silane) of this $C_1$-$C_6$-alkoxysilane used.

However, when a blend of different $C_1$-$C_6$-alkoxysilanes (a) is used during the production of the keratinic treatment, the total molar amount mol(silanes) is summed from each of the individual molar amounts of each $C_1$-$C_6$-alkoxysilane used.

Thus, if several $C_1$-$C_6$-alkoxysilanes (a) are used for producing the composition for treatment of keratinic material, the above equation is expanded by formation of the respective summands to form the equation (G-1'):

$$\text{mol(alkalizing agent)} = \frac{\sum[\text{mol(silanes)} \times n(\text{alkoxy})]}{\text{S-Alkali}} \qquad \text{(G-1')}$$

The variable n(alkoxy) indicates the number of hydrolyzable alkoxy groups per organic $C_1$-$C_6$-alkoxysilane. The number of hydrolyzable alkoxy groups is determined separately for each organic $C_1$-$C_6$-alkoxysilane used. For example, 3-aminopropyltriethoxysilane has 3 hydrolyzable alkoxy groups (3-ethoxy groups). Methyltriethoxysilane likewise has 3 hydrolyzable alkoxy groups (3 ethoxy groups). Metyltrimethoxysilane also has 3 hydrolyzable alkoxy groups (3 methoxy groups).

The variable S-Alkali represents an integer from 50 to 2,000 and is a proportionality factor. This variable specifies the molar ratio in which the organic $C_1$-$C_6$-alkoxysilanes (a) and the alkalizing agent (b) are used. The greater S-Alkali is, the lower the amount of alkali used, wherein this use amount can be varied only in the specific range which is specified by the end points S-Alkali=50 and S-Alkali=2,000.

Computing Example 1

In the production of the composition for treatment of keratinic material, 23.52 g of 3-aminopropyltriethoxysilane ($C_9H_{23}NO_3Si$=221.37 g/mol) and 47.07 g of methyltriethoxysilane ($C_7H_{18}O_3Si$=178.34 g/mol) were first blended together.

23.52 g 3-aminopropyltriethoxysilane (AMEO)=0.106 mol 3-aminopropyltriethoxysilane has 3 hydrolyzable alkoxy groups per molecule 47.07 g methyltriethoxysilane (MTES)=0.264 mol Methyltrimethoxysilane has 3 hydrolyzable alkoxy groups per molecule)

Taking into account the equation (G-1'), the amount of alkalizing agent is calculated as follows:

$$\text{mol(alkalizing agent)} = \frac{\sum[\text{mol(silanes)} \times n(\text{alkoxy})]}{\text{S-Alkali}} \quad (G\text{-}1')$$

with S-Alkali=50-2,000 mol(alkalizing agent)=[(0.106×3)+(0.264×3)]/50=0.0222 mol mol(alkalizing agent)=[(0.106×3)+(0.264×3)]/2,000=0.000555 mol (corresponding to 0.555 mmol)

When the aforementioned amounts of organic $C_1$-$C_6$-alkoxysilanes (a) are used, 0.555 mmol (millimol) to 0.0222 mol of alkalizing agent (b) are to be added in the process according to the invention.

This alkalizing agent (b) can, for example, be 0.555 mmol (millimol) to 0.0222 mol of sodium hydroxide. Furthermore, the alkalizing agent (b) can also, for example, be a mixture of sodium hydroxide and potassium hydroxide, which are used in a total molar amount of 0.555 mmol (millimol) to 0.0222 mol in the reaction or are blended in this amount with the organic $C_1$-$C_6$-alkoxysilanes.

Even if the proportionality factor S-Alkali can represent an integer from 50 to 2,000, it has been found to be very particularly preferred for achieving the object according to the invention if S-Alkali represents an integer from 75 to 1,500, preferably an integer from 90 to 1,000, more preferably an integer from 100 to 700, and most preferably an integer from 150 to 550.

It was observed that the cleaning of the reactor could be carried out especially easily and quickly if the aforementioned preferred and especially preferred quantity ranges were selected for S-Alkali. At the same time, the hair treatment products produced via these processes also had good performance properties on the keratinic material.

In the context of a further especially preferred embodiment, a process according to the invention is characterized in that the organic $C_1$-$C_6$-alkoxysilane(s) (a) is/are blended with an amount of alkalizing agents (b) which corresponds to the molar amount of alkalizing agent determined according to the equation (G-1), where S-Alkali represents an integer from 75 to 1,500, preferably an integer from 90 to 1,000, more preferably an integer from 100 to 700, and most preferably an integer from 150 to 550.

Very particular preference is thus given to a process for producing a composition for treatment of keratinic material, and especially human hair, comprising the blending of (a) one or more organic $C_1$-$C_6$-alkoxysilanes from the group consisting of (3-aminopropyl)triethoxysilane, (3-aminopropyl)trimethoxysilane, (2-aminoethyl)triethoxysilane, (2-aminoethyl)-trimethoxysilane, (3-dimethylaminopropyl)triethoxysilane, (3-dimethylaminopropyl)trimethoxysilane, (2-dimethylaminoethyl) triethoxysilane, (2-dimethylaminoethyl) trimethoxysilane, methyltrimethoxysilane, methyltriethoxysilane, ethyltrimethoxysilane, ethyltriethoxysilane, hexyltrimethoxysilane, hexyltriethoxysilane, octyltrimethoxysilane, octyltriethoxysilane, dodecyltrimethoxysilane, dodecyltriethoxysilane, vinyltrimethoxysilane, vinyltriethoxysilane, tetramethoxysilane, and tetraethoxysilane, with (b) one or more alkalizing agents from the group consisting of sodium hydroxide, potassium hydroxide, lithium hydroxide, magnesium hydroxide, calcium hydroxide, and ammonia, wherein the organic $C_1$-$C_6$-alkoxysilane(s) (a) is/are blended with an amount of alkalizing agent(s) (b) which corresponds to the molar amount of alkalizing agent determined according to the equation (G-1)

$$\text{mol(alkalizing agent)} = \frac{\text{mol(silanes)} \times n(\text{alkoxy})}{\text{S-Alkali}} \quad (G\text{-}1)$$

where mol(alkalizing agent) represents the molar amount of alkalizing agents(s) used, mol(silanes) represents the total molar amount of the $C_1$-$C_6$-alkoxysilanes used in the reaction, n(alkoxy) represents the number of $C_1$-$C_6$-alkoxy groups per $C_1$-$C_6$-alkoxysilane, and S-Alkali is equal to an integer from 50 to 2,000, preferably an integer from 75 to 1,500, more preferably an integer from 90 to 1,000, even more preferably an integer from 100 to 700, and most preferably an integer from 150 to 550.

Quantity Ranges of the Amounts Used of (a) and (b)

The above-described organic $C_1$-$C_6$-alkoxysilanes, and especially their aforementioned preferred and especially preferred representatives, are preferably mixed with one another in specific quantity ranges.

Especially good results were obtained when (a) 40.0 to 99.88 parts by weight, preferably 50 to 98 parts by weight, more preferably 60 to 94 parts by weight, and most preferably 70 to 90 parts by weight of one or more organic $C_1$-$C_6$-alkoxysilanes having one, two, or three silicon atoms, are blended with (b) 0.11 to 2.43 parts by weight, preferably 0.15 to 2.2 parts by weight, more preferably 0.18 to 2.0 parts by weight, even more preferably 0.2 to 1.6 parts by weight, and most preferably 0.25 to 1.2 parts by weight of one or more alkalizing agents.

The specification of the parts by weight of ingredients (a) and (b) indicates the weight ratio in which the two substance classes are blended with one another. In the specification of these amounts and weight ratios, the above-described premise always applies at the same time that the organic $C_1$-$C_6$-alkoxysilane(s) (a) is/are blended with an amount of alkalizing agent(s) (b) which corresponds to the molar amount of alkalizing agent determined according to the equation (G-1).

If one or more organic $C_1$-$C_6$-alkoxysilane(s) (a) is/are blended in a total amount of 40 parts by weight with one or more alkalizing agents (b) in a total amount of 0.11 parts by weight, then, for example, 40 g of organic $C_1$-$C_6$-alkoxysilanes (a) are blended with 0.11 g alkalizing agents (b). A multiple of these weight amounts, such as 80 g of organic $C_1$-$C_6$-alkoxysilanes (a) and 0.22 g of alkalizing agents (b), fall within this ratio condition.

Within the scope of another preferred embodiment, a process according to the invention is characterized by blending (a) 40.0 to 99.88 parts by weight, preferably 50 to 98 parts by weight, more preferably 60 to 94 parts by weight, and most preferably 70 to 90 parts by weight of one or more organic $C_1$-$C_6$-alkoxysilanes having one, two, or three silicon atoms, with (b) 0.11 to 2.43 parts by weight, preferably 0.15 to 2.2 parts by weight, more preferably 0.18 to 2.0 parts by weight, even more preferably 0.2 to 1.6 parts by weight, and most preferably 0.25 to 1.2 parts by weight of one or more alkalizing agents.

Within the scope of another preferred embodiment, a process according to the invention is characterized by blending (a1) 30 to 70 parts by weight of one or more organic $C_1$-$C_6$-alkoxysilanes from the group consisting of methyltrimethoxysilane, methyltriethoxysilane, ethyltrimethoxysilane, ethyltriethoxysilane, hexyltrimethoxysilane, hexyltriethoxysilane, octyltrimethoxysilane, octyltriethoxysilane, dodecyltrimethoxysilane, dodecyltriethoxysilane, vinyltrimethoxysilane, vinyltriethoxysilane, tetramethoxysilane, tetraethoxysilane, with (a2) 10 to 40 parts by weight of one or more organic $C_1$-$C_6$-alkoxysilanes from the group consisting of (3-aminopropyl)triethoxysilane, (3-aminopropyl) trimethoxysilane, (2-aminoethyl)triethoxysilane, (2-aminoethyl)trimethoxysilane, (3-dimethylaminopropyl)triethoxysilane, (3-dimethylaminopropyl) trimethoxysilane, (2-dimethylaminoethyl)triethoxysilane, and (2-dimethylaminoethyl)trimethoxysilane, and (b) 0.11 to 2.43 parts by weight of one or more alkalizing agents from the group consisting of sodium hydroxide, potassium hydroxide, lithium hydroxide, magnesium hydroxide, and calcium hydroxide.

In the case of this especially preferred embodiment, for example, (a1) 30 g to 70 g of one or more organic $C_1$-$C_6$-alkoxysilanes from the group consisting of methyltrimethoxysilane, methyltriethoxysilane, ethyltrimethoxysilane, ethyltri-ethoxysilane, hexyltrimethoxysilane, hexyltriethoxysilane, octyltrimethoxysilane, octyltriethoxysilane, dodecyltrimethoxysilane, dodecyltriethoxysilane, vinyltrimethoxysilane, vinyltriethoxysilane, tetramethoxysilane, tetraethoxysilane, can be blended with (a2) 10 to 40 g of one or more organic $C_1$-$C_6$-alkoxysilanes from the group consisting of (3-aminopropyl) triethoxysilane, (3-aminopropyl) trimethoxysilane, (2-aminoethyl) triethoxysilane, (2-aminoethyl) trimethoxysilane, (3-dimethylaminopropyl) triethoxysilane, (3-dimethylaminopropyl) trimethoxysilane, (2-dimethylaminoethyl) triethoxysilane, and (2-dimethylaminoethyl) trimethoxysilane, and (b) 0.11 to 2.43 g of one or more alkalizing agents from the group consisting of sodium hydroxide, potassium hydroxide, lithium hydroxide, magnesium hydroxide, and calcium hydroxide. A multiple of the grammage of the aforementioned substance classes (a1), (a2), and (b) can also be used, if the ratio conditions according to the invention are complied with.

Blending of (a) and (b)—or (A1), (a2), and (b)—with Water

As soon as the $C_1$-$C_6$-alkoxysilane(s) (a1) and the alkalizing agent (b) come into contact with water, an exothermic hydrolysis reaction takes place according to the following scheme (reaction scheme using the example of 3-aminopropyltriethoxy silane):

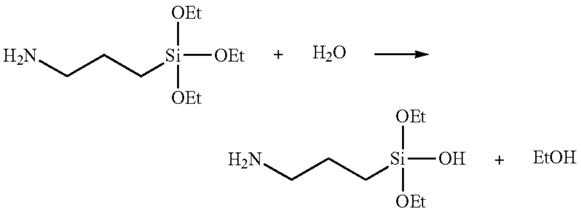

Depending upon the number of hydrolyzable $C_1$-$C_6$-alkoxy groups per silane molecule, the hydrolysis reaction can also occur several times per $C_1$-$C_6$-alkoxysilane used:

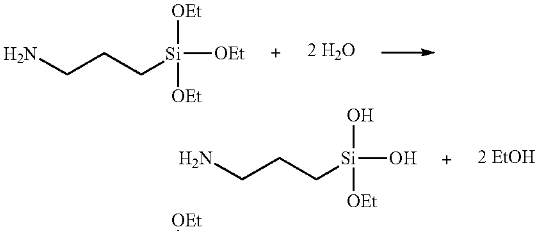

or

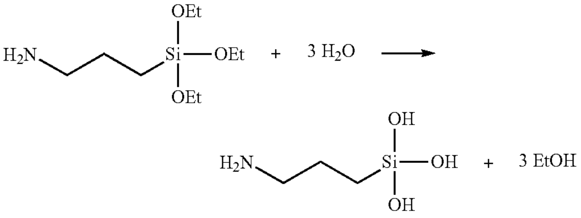

This hydrolysis reaction is accelerated by the presence of the alkalizing agents (b).

For the production of compositions which produce an especially good coating on the keratinic material, it has been found to be explicitly very particularly preferred to use water in a substoichiometric amount. In this case, the amount of water used is below the amount that would theoretically be required to hydrolyze all existing hydrolyzable $C_1$-$C_6$-alkoxy groups on the Si atoms, i.e., the alkoxysilane groups. Very particular preference is therefore given to the partial hydrolysis of the organic $C_1$-$C_6$-alkoxysilanes.

For this reason, it is very particularly preferred if the organic $C_1$-$C_6$-alkoxysilanes (a1) and the alkalizing agent(s) (b) is/are mixed with water (c) in the production process according to the invention. Particular preference is given to blending (a) and (b) with a specific amount of water. Very particular preference is given to using (a) and (b) in the aforementioned parts by weight (or a multiple thereof), and mixing these with 0 to 20 parts by weight, preferably 0.1 to 18 parts by weight, more preferably 1.5 to 16 parts by weight, even more preferably of 3 to 14 parts by weight, and most preferably of 5 to 12 parts by weight of water.

Within the scope of a further especially preferred embodiment, a process according to the invention is characterized by blending (a) and (b) or, as applicable, (a1), (a2), and (b) with (c) 0 to 20 parts by weight, preferably from 0.1 to 18 parts by weight, more preferably 1.5 to 16 parts by weight, even more preferably from 3 to 14 parts by weight, and most preferably from 5 to 12 parts by weight of water.

The water can be added continuously, in portions or directly as the total amount. In order to ensure sufficient temperature control, the reaction mixture is preferably cooled, and/or the addition quantity and speed of the water is adapted. Depending upon the amount of silanes used, the addition and reaction can take place over a period of 2 minutes up to 72 hours.

In the context of a further embodiment, the water (c) can initially also be mixed with the alkalizing agent(s) (b), and this mixture of (b) and (c) can then be blended with the organic $C_1$-$C_6$-alkoxysilanes Use of Solvents (d)

The production process according to the invention makes it possible to dispense with the use of solvents. For various reasons such as for improving the solubility of poorly soluble organic $C_1$-$C_6$-alkoxysilanes and for controlling the exothermicity of the production process it may, however, be advantageous to use one or more solvents other than water in the production of the keratinic treatment composition according to the invention.

In the context of this embodiment, the ingredients (a) and (b), as applicable, (c)—or (a1), (a2), (b) and, as applicable, (c)—especially in the aforementioned preferred and especially preferred parts by weight—are mixed with the solvents (d).

The mixing can take place, for example, by first charging the solvent (d) different from water in a suitable reactor or reaction vessel, and then adding the $C_1$-$C_6$-alkoxysilane(s) (a). The addition can be carried out by dripping or pouring in. Furthermore, it is likewise possible and according to the invention if first at least one organic $C_1$-$C_6$-alkoxysilane (a) is initially provided in the reaction vessel, and then the solvent (d) is added or dripped in. For this purpose, the alkalizing agent (b), which can be present as such or can also be blended beforehand with water, can be added to the mixture of (a) and (d).

A sequential procedure is also possible, i.e., first, the addition of solvent and a first organic $C_1$-$C_6$-alkoxysilane, then the addition of a solvent, and then the addition again of a further organic $C_1$-$C_6$-alkoxysilane.

The solvent is preferably added while stirring.

It may be preferred to select a solvent which at standard pressure (1,013 hPa) has a boiling point of 20 to 90° C., preferably of 30 to 85° C., and very particularly preferably of 40 to 80° C.

Suitable solvents are, for example:

dichloromethane with a boiling point of 40° C. (1,013 mbar)

methanol with a boiling point of 65° C. (1,013 mbar)

tetrahydrofurane with a boiling point of 65.8° C. (1,013 mbar)

ethanol with a boiling point of 78° C. (1,013 mbar)

isopropanol with a boiling point of 82° C. (1,013 mbar)

acetonitrile with a boiling point of 82° C. (1,013 mbar)

Furthermore, very particularly preferred solvents can be selected from the group of mono- or polyvalent $C_1$-$C_{12}$ alcohols. Mono- or polyvalent $C_1$-$C_{12}$ alcohols are compounds having one to twelve carbon atoms, which carry one or more hydroxy groups. Further functional groups different from the hydroxyl groups are, in accordance with the invention, not present in $C_1$-$C_{12}$ alcohols. The $C_1$-$C_{12}$ alcohols may be aliphatic or aromatic.

Methanol, ethanol, n-propanol, isopropanol, n-pentanol, n-hexanol, benzyl alcohol, 2-phenylethanol, 1,2-propanediol, 1,3-propanediol, and glycerol can be mentioned, for example, as suitable $C_1$-$C_{12}$ alcohols. Very particularly suitable $C_1$-$C_{12}$ alcohols are methanol, ethanol, and isopropanol.

Within the scope of a further especially preferred embodiment, a process according to the invention is characterized by blending (a) and (b)—or, as applicable, (a1), (a2), and (b)—with (d) 0 to 60 parts by weight, preferably 0 to 30 parts by weight, more preferably 0 to 20 parts by weight, and most preferably 0 parts by weight of one or more solvents from the group consisting of poly-$C_1$-$C_6$-alkylene glycols, 1,2-propylene glycol, 1,3-propylene glycol, 1,2-butylene glycol, dipropylene glycol, ethanol, isopropanol, diethylene glycol monoethyl ether, glycerol, phenoxyethanol, and benzyl alcohol.

After the hydrolysis or condensation reaction has ended, the solvent can be removed again. The removal can be effected by distillation under reduced pressure—for example, using a rotary evaporator. Further work, however, has shown that it may also be advantageous for the solvent or solvents to be left out in the mixture of organic $C_1$-$C_6$-alkoxysiloxanes.

Steps in the Production Process

As already described above, the blending of substance classes (a) and (b) or (a1), (a2), and (b) as well as, where applicable, (c) and, where applicable, (d) can take place in different ways and in a different sequence.

A process comprising the following steps has been found to be very especially well suited for achieving the object according to the invention:

(1) providing one or more organic $C_1$-$C_6$-alkoxysilanes having one, two, or three silicon atoms (a) in a reaction vessel,
(2) mixing one or more alkalizing agents (b) with water (c),
(3) blending the organic $C_1$-$C_6$-alkoxysilanes (a) with the mixture of alkalizing agent (b) and water (c), as applicable with stirring and/or heating of the mixture in the reaction vessel to a temperature of 30 to 90° C.,
(4) where applicable, stirring the mixture produced in step (3) for a period of 1 minute to 4 hours, and preferably of 1 minute to 1 hour,
(5) filling the mixture of (a) and (b) and (c) from the reaction vessel.

Within the context of a further embodiment, a process according to the invention is particularly preferred which comprises the following steps:

(1) providing one or more organic $C_1$-$C_6$-alkoxysilanes having one, two, or three silicon atoms (a) in a reaction vessel,
(2) mixing one or more alkalizing agents (b) with water (c),
(3) blending the organic $C_1$-$C_6$-alkoxysilanes (a) with the mixture of alkalizing agent (b) and water (c), as applicable with stirring and/or heating of the mixture in the reaction vessel to a temperature of 30 to 90° C.,
(4) where applicable, stirring the mixture produced in step (3) for a period of 1 minute to 4 hours, and preferably of 1 minute to 1 hour,
(5) filling the mixture of (a) and (b) and (c) from the reaction vessel.

In the context of a further embodiment, particular preference is given to a process according to the invention comprising the following steps in the indicated order:

(1) providing one or more organic $C_1$-$C_6$-alkoxysilanes having one, two, or three silicon atoms (a) in a reaction vessel,
(2) mixing one or more alkalizing agents (b) with water (c), (3) blending the organic $C_1$-$C_6$-alkoxysilanes (a) with the mixture of alkalizing agent (b) and water (c), as applicable with stirring and/or heating of the mixture in the reaction vessel to a temperature of 30 to 90° C., (4) where applicable, stirring the mixture produced in step (3) for a period of 1 minute to 4 hours, and preferably of 1 minute to 1 hour, (5) filling the mixture of (a) and (b) and (c) from the reaction vessel.

The mixture produced in this way of (a) and (b) and (c) and, as applicable, (d) can alternatively also be referred to as a silane blend.

As an optional step, the process according to the invention can also comprise the addition of one or more cosmetic ingredients. The further ingredient(s) can be added, for example, after one of steps (1), (2), (3), (4), and/or (5).

The cosmetic ingredients which can optionally be used in step can be all suitable components for imparting further positive properties to the agent. For example, cosmetic ingredients from the group of thickening or film-forming polymers, the surface-active compounds from the group of nonionic, cationic, anionic or zwitterionic/amphoteric surfactants, the coloring compounds from the group of the pigments, the direct dyes, the oxidation dye precursors, the fatty components from the group of $C_8$-$C_{30}$ fatty alcohols, the hydrocarbon compounds, fatty acid esters, the acids and bases associated with the group of pH regulators, the perfumes, the preservatives, the plant extracts, and the protein hydrolyzates can be added.

Agent for Treating Keratinic Material

The process described above allows the production of pre-hydrolyzed or condensed silane blends which, when applied to keratinic material, exhibit extraordinarily good performance.

In principle, the keratinic treatment compositions produced by means of this process can be used for various purposes, e.g., as compositions for coloring keratinic material, as compositions for the care of keratinic material, or as compositions for changing the shape of keratinic material.

A further subject matter of the present finding is a composition for treatment of keratinic material, and especially human hair, which has been produced by a process as disclosed in detail in the description of the first subject matter of the invention.

In a further very particularly preferred embodiment, a composition according to the invention is characterized in that it is a composition for coloring keratinic material, for the care of keratinic material, or for changing the shape of keratinic material.

The compositions produced are explicitly very particularly well suited for use in a dyeing process.

When used as a coloring agent, the composition can be added, for example, in steps (1), (2), (3), (4), and/or (5), or, before or after one of these steps, at least one coloring compound can be added, wherein the coloring compound can be selected from the group consisting of the pigments, the direct dyes, and/or the oxidation dye precursors. In this case, a composition for coloring keratinic material can be obtained which also contains, in addition to the prehydrolyzed/condensed $C_1$-$C_6$-alkoxysilanes, the coloring compound(s).

Use of the Composition for Treatment of Keratinic Material

A further subject matter of the present invention is the use of a composition produced by a process of the first subject matter of the invention for the treatment of keratinic material—especially for coloring keratinic material, and especially for coloring human hair.

When using the products produced by the process according to the invention in a dyeing process, one or more coloring compounds can be used. As described above, the coloring compound(s) can be added to the reaction mixture as cosmetic ingredients during the production process, or else be made available to the user as an ingredient of a separately packaged preparation.

The coloring compound or compounds can preferably be selected from the group consisting of the pigments, the direct dyes, the oxidation dyes, the photochromic dyes, and the thermochromic dyes—especially preferably consisting of pigments and/or direct dyes.

Pigments in the sense of the present invention are understood to mean dyeing compounds which have a solubility of less than 0.5 g/L, preferably of less than 0.1 g/L, and even more preferably of less than 0.05 g/L, at 25° C. in water. The water solubility can be determined, for example, by means of the method described below: 0.5 g of the pigment is weighed into a beaker. A stir bar is added. Then one liter of distilled water is added. This mixture is heated to 25° C. while stirring with a magnetic stirrer for one hour. If still undissolved components of the pigment are visible in the mixture after this period, the solubility of the pigment is below 0.5 g/L. If the pigment-water mixture cannot be visually assessed due to the high intensity of the pigment that may be finely dispersed, the mixture is filtered. If a portion of undissolved pigments remains on the filter paper, the solubility of the pigment is below 0.5 g/L.

Suitable dye pigments may be of inorganic and/or organic origin.

In a preferred embodiment, the agent according to the invention is characterized in that it contains at least one dyeing compound from the group of the inorganic and/or organic pigments.

Preferred color pigments are selected from synthetic or natural inorganic pigments. Inorganic color pigments of natural origin can be produced, for example, from chalk, ocher, umbra, green soil, burnt Sienna, or graphite. Furthermore, black pigments such as, for example, iron oxide black, chromatic pigments such as, for example, ultramarine or iron oxide red, and also fluorescent or phosphorescent pigments, can be used as inorganic color pigments.

Colored metal oxides, hydroxides, and oxide hydrates, mixed phase pigments, sulfur-containing silicates, silicates, metal sulfides, complex metal cyanides, metal sulfates, chromates, and/or molybdates are particularly suitable. Particularly preferred color pigments are black iron oxide (CI 77499), yellow iron oxide (CI 77492), red and brown iron oxide (CI 77491), manganese violet (CI 77742), ultramarine (sodium aluminum sulphosilicates, CI 77007, Pigment Blue 29), chromium oxide hydrate (CI 77289), iron blue (ferric ferrocyanide, CI 77510), and/or carmine (cochineal).

Dyeing compounds from the group of the pigments which are also particularly preferred according to the invention are colored pearlescent pigments. These are usually based upon mica and may be coated with one or more metal oxides. Mica is a phyllosilicate. The most important representatives of these silicates are muscovite, phlogopite, paragonite, biotite, lepidolite, and margarite. In order to produce the pearlescing pigments in conjunction with metal oxides, mica, and primarily muscovite or phlogopite, is coated with a metal oxide.

As an alternative to natural mica, synthetic mica coated with one or more metal oxides(s) can also be used as a pearlescent pigment. Particularly preferred pearlescent pigments are based upon natural or synthetic mica and are coated with one or more of the aforementioned metal oxides.

The color of the respective pigments can be varied by varying the layer thickness of the metal oxide(s).

In a further preferred embodiment, a composition according to the invention is characterized in that it (b) contains at least one dyeing compound from the group of the pigments selected from the group consisting of colored metal oxides, metal hydroxides, metal oxide hydrates, silicates, metal sulfides, complex metal cyanides, metal sulphates, bronze pigments, and/or from mica-based dyeing compounds which are coated with at least one metal oxide and/or one metal oxychloride.

In another preferred embodiment, a composition according to the invention is characterized in that it (b) contains at least one coloring compound selected from mica-based pigments, which are coated with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288), and/or iron blue (ferric ferrocyanide, CI 77510).

Examples of particularly suitable color pigments are commercially available, for example, under the trade names, Rona®, Colorona®, Xirona®, Dichrona®, and Timiron® from the company Merck, Ariabel® and Unipure® from the company Sensient, Prestige® from the company Eckart Cosmetic Colors, and Sunshine® from the company Sunstar.

Very particularly preferred color pigments with the trade name, Colorona®, are, for example:

Colorona Copper, Merck, MICA, CI 77491 (IRON OXIDES)

Colorona Passion Orange, Merck, mica, CI 77491 (IRON OXIDES), alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)

Colorona Carmine Red, Merck, MICA, TITANIUM DIOXIDE, CARMINE

Colorona Blackstar Green, Merck, MICA, CI 77499 (IRON OXIDES)

Colorona Bordeaux, Merck, MICA, CI 77491 (IRON OXIDES)

Colorona Bronze, Merck, MICA, CI 77491 (IRON OXIDES)

Colorona Bronze Fine, Merck, MICA, CI 77491 (IRON OXIDES)

Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA

Colorona Sienna, Merck, MICA, CI 77491 (IRON OXIDES)

Colorona Precious Gold, Merck, mica, CI 77891 (titanium dioxide), silica, CI 77491 (IRON OXIDES), tin oxide Colorona Sun Gold Sparkle MP 29, Merck, MICA, TITANIUM DIOXIDE, IRON OXIDES, MICA, CI 77891, CI 77491 (EU)

Colorona Mica Black, Merck, CI 77499 (iron oxides), mica, CI 77891 (titanium dioxide)

Colorona Bright Gold, Merck, mica, CI 77891 (titanium dioxide), CI 77491 (iron oxides)

Colorona Blackstar Gold, Merck, MICA, CI 77499 (IRON OXIDES)

Additional particularly preferred color pigments with the trade name, Xirona®, are, for example:

Xirona Golden Sky, Merck, silica, CI 77891 (titanium dioxide), tin oxide

Xirona Caribbean Blue, Merck, mica, CI 77891 (titanium dioxide), silica, tin oxide Xirona Kiwi Rose, Merck, silica, CI 77891 (titanium dioxide), tin oxide Xirona Magic Mauve, Merck, silica, CI 77891 (titanium dioxide), tin oxide.

In addition, particularly preferred color pigments with the trade name, Unipure®, are, for example:

Unipure Red LC 381 EM, Sensient CI 77491 (iron oxides), silica

Unipure Black LC 989 EM, Sensient, CI 77499 (iron oxides), silica

Unipure Yellow LC 182 EM, Sensient, CI 77492 (iron oxides), silica

In the context of another embodiment, the agent according to the invention or the preparation according to the invention can also additionally contain one or more dyeing compounds from the group of organic pigments.

The organic pigments according to the invention are correspondingly insoluble organic dyes or color lakes which may be selected, for example, from the group of nitroso, nitro, azo, xanthene, anthraquinone, isoindolinone, isoindoline, quinacridone, perinone, perylene, diketopyrrolopyorrole, indigo, thioindido, dioxazine, and/or triarylmethane compounds.

Particularly well-suited organic pigments can for example include carmine, quinacridone, phthalocyanine, sorghum, blue pigments with the Color Index numbers CI 42090, CI 69800, CI 69825, CI 73000, CI 74100, or CI 74160, yellow pigments with the Color Index numbers CI 11680, CI 11710, CI 15985, CI 19140, CI 20040, CI 21100, CI 21108, CI 47000, or CI 47005, green pigments with the Color Index numbers CI 61565, CI 61570, or CI 74260, orange pigments with the Color Index numbers CI 11725, CI 15510, CI 45370, or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

In another especially preferred embodiment, a composition according to the invention is characterized in that it contains at least one coloring compounds from the group of organic pigments, which is selected from the group consisting of carmine, quinacridone, phthalocyanine, sorghum, blue pigments with the Color Index numbers CI 42090, CI 69800, CI 69825, CI 73000, CI 74100, or CI 74160, yellow pigments with the Color Index numbers CI 11680, CI 11710, CI 15985, CI 19140, CI 20040, CI 21100, CI 21108, CI 47000, or CI 47005, green pigments with the Color Index numbers CI 61565, CI 61570, or CI 74260, orange pigments with the Color Index numbers CI 11725, CI 15510, CI 45370, or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

The organic pigment can also be a color lacquer. The term, color lacquer, in the sense of the invention is understood to mean particles which comprise a layer of absorbed dyes, with the unit consisting of particles and dye being insoluble under the above-mentioned conditions. The particles may, for example, be inorganic substrates which may be aluminum, silica, calcium borosilicate, calcium aluminum borosilicate, or aluminum.

For example, the alizarin color lacquer can be used as the color lacquer.

Due to their excellent light and temperature resistance, the use of the aforementioned pigments in the agent according to the invention is particularly preferred. It is further preferred if the pigments used have a certain particle size. This particle size on the one hand leads to a uniform distribution of the pigments in the polymer film formed and, on the other, avoids a rough hair or skin feel after the application of the cosmetic agent. It is therefore advantageous according to the invention if the at least one pigment has a mean particle size $D_{50}$ of 1.0 to 50 μm, preferably of 5.0 to 45 μm, preferably of 10 to 40 μm, and in particular of 14 to 30 μm. The mean particle size $D_{50}$ can be determined, for example, using dynamic light scattering (DLS).

The pigment or pigments can be used in an amount of 0.001 to 20 wt %, and especially of 0.05 to 5 wt %, in each case relative to the total weight of the composition or preparation according to the invention.

The compositions according to the invention can also contain one or more direct dyes as dyeing compounds. The direct dyes are dyes which attach directly to the hair and require no oxidative process to form the color. Direct dyes are usually nitrophenylenediamines, nitroaminophenols, azo dyes, anthraquinones, triarylmethane dyes, or indophenols.

The direct dyes in the sense of the present invention have a solubility in water (760 mmHg) at 25° C. of more than 0.5 g/L and are therefore not to be regarded as pigments. In the sense of the present invention, the direct dyes preferably have a solubility in water (760 mmHg) at 25° C. of more than 1.0 g/L. In the sense of the present invention, the direct dyes particularly preferably have a solubility in water (760 mmHg) at 25° C. of more than 1.5 g/L.

Direct dyes can be divided into anionic, cationic, and non-ionic direct dyes.

In a further preferred embodiment, an agent according to the invention is characterized in that it contains at least one anionic, cationic, and/or non-ionic direct dye as a dyeing compound.

In a further preferred embodiment, an agent according to the invention is characterized in that it contains at least one anionic, cationic, and/or non-ionic direct dye.

Suitable cationic direct dyes are for example Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, Basic Red 76

In particular, non-ionic nitro dyes and quinone dyes and neutral azo dyes, for example, can be used as non-ionic direct dyes. Suitable non-ionic direct dyes are the compounds known under the international names or trade names, HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and also 1,4-diamino-2-nitrobenzene, 2-amino-4-nitrophenol, 1,4-bis(2-hydroxyethyl)amino-2-nitrobenzene, 3-nitro-4-(2-hydroxy-ethyl)aminophenol, 2-(2-hydroxy-ethyl)amino-4,6-dinitrophenol, 4-[(2-hydroxyethyl)amino]-3-nitro-1-methylbenzene, 1-amino-4-(2-hydroxyethyl) amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Anionic direct dyes are also referred to as acid dyes. Acid dyes mean direct dyes that have at least one carboxylic acid group (—COOH) and/or a sulfonic acid group ($—SO_3H$). Depending upon the pH, the protonated forms (—COOH, $—SO_3H$) of the carboxylic acid or sulfonic acid groups are present in equilibrium with their deprotonated forms (—COO—, $—SO_3—$). The proportion of the protonated forms increases with decreasing pH. If direct dyes are used in the form of their salts, the carboxylic acid groups or sulfonic acid groups are present in the deprotonated form and are neutralized with corresponding stoichiometric equivalents of cations in order to maintain electroneutrality. Acid dyes according to the invention can also be used in the form of their sodium salts and/or their potassium salts.

The acid dyes in the sense of the present invention have a solubility in water (760 mmHg) at 25° C. of more than 0.5 g/L and are therefore not to be regarded as pigments. In the sense of the present invention, the acid dyes preferably have a solubility in water (760 mmHg) at 25° C. of more than 1.0 g/L.

The alkaline earth salts (for example, calcium salts and magnesium salts) or aluminum salts of acid dyes often have poorer solubility than the corresponding alkali salts. If the solubility of these salts is below 0.5 g/L (25° C., 760 mmHg), they do not fall under the definition of a direct dye.

An essential feature of the acid dyes is their ability to form anionic charges, with the carboxylic acid groups or sulfonic acid groups responsible for this usually being linked to various chromophore systems. Suitable chromophore systems are found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

For example, as particularly well-suited acid dyes, one or more compounds can be selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Echtrot D, FD&C Red Nr.2, Food Red 9, Naphtholrot S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no. 2, CI 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patentblau AE, Amidoblau AE, Erioglaucin A, CI 42090, CI Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, CI 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

The water solubility of the anionic direct dyes can be determined, for example, in the following manner. 0.1 g of the anionic direct dye is placed in a beaker. A stirring bar is added. Then, 100 mL of water are added. This mixture is heated to 25° C. on a magnetic stirrer, while stirring. The mixture is stirred for 60 minutes. Thereafter, the aqueous mixture is visually assessed. If there are still undissolved residues, the amount of water is increased—for example, in steps of 10 mL. Water is added until the amount of dye used has dissolved completely. If the dye-water mixture cannot be visually assessed due to the high intensity of the dye, the mixture is filtered. If a proportion of undissolved dyes remains on the filter paper, the solubility test is repeated with a larger amount of water. If 0.1 g of the anionic direct dye dissolves in 100 mL of water at 25° C., the solubility of the dye is 1.0 g/L.

Acid Yellow 1 carries the name 8-hydroxy-5,7-dinitro-2-naphthalenesulfonic acid disodium salt and has a solubility in water of at least 40 g/L (25° C.).

Acid Yellow 3 is a mixture of the sodium salts of mono and sis-sulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid; its water solubility is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid, and is readily soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trisodium salt of 7-hydroxy-8-[(E)-(4-sulfonato-1-naphthyl)diazenyl)]-1,3-naphthalenedisulfonate and has a very high water solubility of more than 20 wt %.

Acid Red 33 is the disodium salt of 5-amino-4-hydroxy-3-(phenylazo)-naphthalene-2,7-disulfonate; its water solubility is 2.5 g/L (25° C.).

Acid Red 92 is the disodium salt of 3,4,5,6-tetrachloro-2-(1,4,5,8-tetrabromo-6-hydroxy-3-oxanthene-9-yl) benzoic acid, the water solubility of which is specified as greater than 10 g/L (25° C.).

Acid Blue 9 is the disodium salt of 2-({4-[N-ethyl(3-sulfonatobenzyl]amino]phenyl} {4-[(N-ethyl(3-sulfonatobenzyl)imino]-2,5-cyclohexadien-1-ylidene}methyl)-benzenesulfonate and has a water solubility of more than 20 wt % (25° C.).

Furthermore, thermochromic dyes can also be used. Thermochromism involves the property of reversibly or irreversibly changing the color of a material depending upon the temperature. This can take place both by changing the intensity and/or by changing the wavelength maximum.

Finally, it is also possible to use photochromic dyes. Photochromism involves the property of reversibly or irreversibly changing the color of a material, depending upon the irradiation with light, and in particular UV light. This can take place both by changing the intensity and/or by changing the wavelength maximum.

With respect to the additional preferred embodiments of the compositions according to the invention and the use according to the invention, what has been said about the process according to the invention applies mutatis mutandis.

What is claimed is:

1. A process for producing a composition for treatment of keratinic material, comprising: blending (a) one or more organic $C_1$-$C_6$-alkoxysilanes having one, two, or three silicon atoms, with (b) one or more alkalizing agents, wherein the organic $C_1$-$C_6$-alkoxysilanes (a) are blended with an amount of alkalizing agent (b) corresponding to the molar amount of alkalizing agent determined according to the equation (G-1)

$$\text{mol(alkalizing agent)} = \frac{\text{mol(silanes)} \times n\text{(alkoxy)}}{\text{S-Alkali}} \quad \text{(G-1)}$$

where mol(alkalizing agent) represents the total molar amount of the alkalizing agents used, mol(silanes) represents the total molar amount of the $C_1$-$C_6$-alkoxysilanes used, n(alkoxy) represents the number of $C_1$-$C_6$-alkoxy groups per $C_1$-$C_6$-alkoxysilane, and S-Alkali represents an integer from 50 to 2,000.

2. The process according to claim 1, wherein the one or more organic $C_1$-$C_6$-alkoxysilanes (a) is/are selected from the group consisting of:

(3-aminopropyl)triethoxysilane,
(3-aminopropyl)trimethoxysilane,
(2-aminoethyl)triethoxysilane,
(2-aminoethyl)trimethoxysilane,
(3-dimethylaminopropyl)triethoxysilane,
(3-dimethylaminopropyl)trimethoxysilane,
(2-dimethylaminoethyl)triethoxysilane,
(2-dimethylaminopropyl)trimethoxysilane,
methyltrimethoxysilane,
methyltriethoxysilane,
ethyltrimethoxysilane,
ethyltriethoxysilane,
hexyltrimethoxysilane,
hexyltriethoxysilane,
octyltrimethoxysilane,
octyltriethoxysilane,
dodecyltrimethoxysilane,
dodecyltriethoxysilane,
vinyltrimethoxysilane,
vinyltriethoxysilane,
tetramethoxysilane, and
tetraethoxysilane.

3. The process according to claim 1, wherein the organic $C_1$-$C_6$-alkoxysilane(s) (a) is/are blended with one or more alkalizing agents (b) selected from the group consisting of: sodium hydroxide, potassium hydroxide, lithium hydroxide, magnesium hydroxide, calcium hydroxide, and ammonia.

4. The process according to claim 1, wherein the organic $C_1$-$C_6$-alkoxysilanes (a) are blended with an amount of alkalizing agent (b) which corresponds to the molar amount of alkalizing agent determined according to the equation (G-1), wherein S-Alkali represents an integer from 75 to 1,500.

5. The process according to claim 1, wherein the organic $C_1$-$C_6$-alkoxysilanes (a) are blended with an amount of alkalizing agent (b) which corresponds to the molar amount of alkalizing agent determined according to the equation (G-1), wherein S-Alkali represents an integer from 90 to 1,000.

6. The process according to claim 1, wherein the organic $C_1$-$C_6$-alkoxysilanes (a) are blended with an amount of alkalizing agent (b) which corresponds to the molar amount of alkalizing agent determined according to the equation (G-1), wherein S-Alkali represents an integer from 100 to 700.

7. The process according to claim 1, wherein the organic $C_1$-$C_6$-alkoxysilanes (a) are blended with an amount of alkalizing agent (b) which corresponds to the molar amount of alkalizing agent determined according to the equation (G-1), wherein S-Alkali represents an integer from 150 to 550.

8. The process according to claim 1, wherein the one or more organic $C_1$-$C_6$-alkoxysilanes having one, two, or three silicon atoms is present in an amount of 40.0 to 99.88 parts by weight, and the one or more alkalizing agents is present in amounts of 0.11 to 2.43 parts by weight.

9. The process according to claim 1, wherein the one or more organic $C_1$-$C_6$-alkoxysilanes having one, two, or three silicon atoms is present in an amount of 60 to 94 parts by weight, and the one or more alkalizing agents is present in amounts of 0.15 to 2.2 parts by weight.

10. The process according to claim 1, wherein the one or more organic $C_1$-$C_6$-alkoxysilanes having one, two, or three silicon atoms is present in an amount of 70 to 90 parts by weight, and the one or more alkalizing agents is present in amounts of 0.18 to 2.0 parts.

11. The process according to claim 1, wherein the composition comprises (a1) 30 to 70 parts by weight of one or more organic $C_1$-$C_6$-alkoxysilanes from the group consisting of methyltrimethoxysilane, methyltriethoxysilane, ethyltrimethoxysilane, ethyltriethoxysilane, hexyltrimethoxysilane, hexyltriethoxysilane, octyltrimethoxysilane, octyltriethoxysilane, dodecyltrimethoxysilane, dodecyltriethoxysilane, vinyltrimethoxysilane, vinyltriethoxysilane, tetramethoxysilane, tetraethoxysilane, with (a2) 10 to 40 parts by weight of one or more organic $C_1$-$C_6$-alkoxysilanes from the group consisting of (3-aminopropyl) triethoxysilane, (3-aminopropyl) trimethoxysilane, (2-aminoethyl) triethoxysilane, (2-aminoethyl) trimethoxysilane, (3-dimethylaminopropyl) triethoxysilane, (3-dimethylaminopropyl) trimethoxysilane, (2-dimethylaminoethyl) triethoxysilane, and (2-dimethylaminoethyl) trimethoxysilane, and (b) 0.11 to 2.43 parts by weight of one or more alkalizing agents from the group consisting of sodium hydroxide, potassium hydroxide, lithium hydroxide, magnesium hydroxide, and calcium hydroxide.

12. The process according to claim 1, wherein the one or more organic $C_1$-$C_6$-alkoxysilanes (a) and/or the at least one alkalizing agent(s) (b) is mixed with water such that the water comprises 0 to 20 parts by weight.

13. The process according to claim 1, wherein the one or more organic $C_1$-$C_6$-alkoxysilanes (a) and/or the at least one alkalizing agent(s) (b) is mixed with water such that the water comprises 0.1 to 18 parts by weight.

14. The process according to claim 1, wherein the one or more organic $C_1$-$C_6$-alkoxysilanes (a) and/or the at least one alkalizing agent(s) (b) is mixed with water such that the water comprises 1.5 to 16 parts by weight.

15. The process according to claim 1, wherein the one or more organic $C_1$-$C_6$-alkoxysilanes (a) and/or the at least one alkalizing agent(s) (b) is mixed with water such that the water comprises 3 to 14 parts by weight.

16. The process according to claim 1, wherein the one or more organic $C_1$-$C_6$-alkoxysilanes (a) and/or the at least one alkalizing agent(s) (b) is mixed with water such that the water comprises of 5 to 12 parts by weight of water.

17. The process according to claim 1, wherein the one or more organic $C_1$-$C_6$-alkoxysilanes (a) and/or the at least one alkalizing agent(s) (b) is mixed with one or more solvents selected from the group consisting of poly-$C_1$-$C_6$-alkylene glycols, 1,2-propylene glycol, 1,3-propylene glycol, 1,2-butylene glycol, dipropylene glycol, ethanol, isopropanol, diethylene glycol monoethyl ether, glycerol, phenoxyethanol, and benzyl alcohol.

18. The process according to claim 1, wherein the one or more solvents comprises 0 to 60 parts by weight.

19. The process according to one claim 1, further comprising the following steps:

(1) providing one or more organic $C_1$-$C_6$-alkoxysilanes having one, two, or three silicon atoms (a) in a reaction vessel, (2) mixing one or more alkalizing agents (b) with water (c), (3) blending of the organic $C_1$-$C_6$-alkoxysilanes (a) with the mixture of alkalizing agent (b) and water (c), as applicable with stirring and/or heating of the mixture in the reaction vessel to a temperature of 30 to 90° C., (4) where applicable, stirring the mixture produced in step (3) for a period of 1 minute to 4 hours, and preferably of 1 minute to 1 hour, (5) filling the mixture of (a) and (b) and (c) from the reaction vessel.

20. A composition for treatment of keratinic material, produced by a process according to one of claim 1.

* * * * *